(12) United States Patent
Houze et al.

(10) Patent No.: US 8,110,565 B2
(45) Date of Patent: *Feb. 7, 2012

(54) ENHANCED DRUG DELIVERY IN TRANSDERMAL SYSTEMS

(75) Inventors: David Houze, Coconut Grove, FL (US); Viet Nguyen, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 308 days.

This patent is subject to a terminal disclaimer.

(21) Appl. No.: 11/979,263

(22) Filed: Oct. 31, 2007

(65) Prior Publication Data

US 2008/0167280 A1    Jul. 10, 2008

Related U.S. Application Data

(63) Continuation of application No. 10/330,281, filed on Dec. 30, 2002, now Pat. No. 7,456,159, which is a continuation of application No. PCT/US02/16579, filed on Jun. 18, 2002.

(60) Provisional application No. 60/298,381, filed on Jun. 18, 2001.

(51) Int. Cl.
  *A01N 43/00* (2006.01)
  *A01N 45/00* (2006.01)
  *A61K 31/33* (2006.01)
  *A61K 31/56* (2006.01)

(52) U.S. Cl. ....................................... 514/183; 514/171

(58) Field of Classification Search .................. 514/171, 514/183

See application file for complete search history.

(56) References Cited

U.S. PATENT DOCUMENTS

| 4,529,601 A | 7/1985 | Broberg et al. |
| 4,584,355 A | 4/1986 | Blizzard et al. |
| 4,585,452 A | 4/1986 | Sablotsky |

(Continued)

FOREIGN PATENT DOCUMENTS

CL    49-2005    1/1994

(Continued)

OTHER PUBLICATIONS

Yamada K and Tojo K, "Bioconversion of estradiol esters in the skin of various animal models in vitro," European Journal of Pharmaceutics and Biopharmaceutics, 1997, 43(3), 253-258.*

(Continued)

*Primary Examiner* — San-Ming Hui
*Assistant Examiner* — Paul Zarek
(74) *Attorney, Agent, or Firm* — Foley & Lardner LLP

(57) ABSTRACT

A composition for transdermal administration resulting from an admixture includes: a therapeutically effective amount of a drug that includes a parent drug and a prodrug; and a pharmaceutically acceptable carrier, wherein the parent drug and prodrug are individually present in an amount sufficient for a pharmacological effect. In a preferred embodiment, the admixture includes: a therapeutically effective amount of a pharmaceutically active agent that includes a corresponding steroid and a steroid derivative; and a carrier for the pharmaceutically active agent. The steroid and the corresponding steroid derivative are present in a weight ratio of 10:1 to 1:10 steroid:corresponding steroid derivative. In a preferred embodiment ratio is 6:1 to 1:6. In a preferred embodiment, the corresponding steroid derivative is a steroid ester. In another preferred embodiment, the carrier is a polymer that includes a pressure-sensitive adhesive. In another preferred embodiment, the parent drug is an ACE inhibitor such as ramipril and the prodrug is an ACE inhibitor prodrug such as ramipril ethyl and/or methyl ester.

23 Claims, 9 Drawing Sheets

U.S. PATENT DOCUMENTS

| | | | |
|---|---|---|---|
| 4,585,836 | A | 4/1986 | Homan et al. |
| 4,591,622 | A | 5/1986 | Blizzard et al. |
| 4,655,767 | A | 4/1987 | Woodard et al. |
| 4,906,169 | A | 3/1990 | Chien et al. |
| 5,422,119 | A | 6/1995 | Casper |
| 5,474,783 | A | 12/1995 | Miranda et al. |
| 5,633,242 | A | 5/1997 | Oettel et al. |
| 5,656,386 | A | 8/1997 | Scherer et al. |
| 5,711,962 | A | 1/1998 | Cordes et al. |
| 5,770,219 | A | 6/1998 | Chiang et al. |
| 5,780,050 | A | 7/1998 | Jain et al. |
| 5,811,117 | A | 9/1998 | Hashimoto et al. |
| 5,849,729 | A | 12/1998 | Zoumas et al. |
| 5,898,032 | A | 4/1999 | Hodgen |
| 5,958,446 | A | 9/1999 | Miranda et al. |
| 6,024,974 | A | 2/2000 | Li |
| 6,143,319 | A | 11/2000 | Meconi et al. |
| 6,149,935 | A | 11/2000 | Chiang et al. |
| 6,153,216 | A | 11/2000 | Cordes et al. |
| 6,221,383 | B1 | 4/2001 | Miranda et al. |
| 6,303,141 | B1 | 10/2001 | Fischer et al. |
| 6,368,616 | B1 | 4/2002 | Doi |
| 7,456,159 | B2 | 11/2008 | Houze et al. |
| 7,846,916 | B2 | 12/2010 | Houze |
| 7,867,986 | B2 | 1/2011 | Houze |
| 7,879,831 | B2 | 2/2011 | Houze |
| 2003/0152613 | A1 | 8/2003 | Houze |
| 2003/0152614 | A1 | 8/2003 | Houze |
| 2003/0152615 | A1 | 8/2003 | Houze |
| 2008/0167365 | A1 | 7/2008 | Houze et al. |

FOREIGN PATENT DOCUMENTS

| | | |
|---|---|---|
| CL | 50-1996 | 1/1995 |
| EP | 0 279 977 A2 | 8/1988 |
| EP | 0 294 601 B1 | 1/1993 |
| EP | 0 371 431 B1 | 6/1995 |
| WO | WO 90/06736 A1 | 6/1990 |
| WO | WO 94/10986 A1 | 5/1994 |
| WO | WO 94/16709 A2 | 8/1994 |
| WO | WO 98/51283 A1 | 11/1998 |
| WO | WO-99/15156 A1 | 4/1999 |
| WO | WO 99/66907 | 12/1999 |
| WO | WO 01/02015 A1 | 1/2001 |

OTHER PUBLICATIONS

Bundgard, H., "Design of Prodrugs", *Elsevier*, pp. 7-9, 21-24 (1985).

"Burger's Medicinal Chemistry and Drug Discovery", Fifth Ed. vol. 1: Principles and Practice, pp. 172-178 and pp. 949-982 (1995).

Mashkovsky, M.D., The Medicaments, Guidelines for Medicinal Doctors, vol. 1, (2001), 2 pgs., translation provided.

Remingtons Pharmaceutical Sciences, 18th ed., pp. 1596-1602 (1990).

Silverman, R.B., The Organic Chemistry of Drug Design and Drug Action, pp. 352-401, Academic Press, San Diego, Calif. (1992).

Sobieski, L.A. et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989).

Vaughan, C.D., "Using Solubility Parameters in Cosmetics Formulation," *J. Soc. Cosmet. Chem.*, vol. 36, pp. 319-333 (1985).

Examiner's Answer to Appeal Brief, Issued Oct. 16, 2008, in U.S. Appl. No. 10/330,361, 8 pages.

Examiner's Answer to Appeal Brief, issued Oct. 16, 2008, in U.S. Appl. No. 10/330,360, 10 pages.

Examiner's Answer to Appeal Brief, issued Oct. 16, 2008,. In U.S. Appl. No. 10/330,279, 9 pages.

Examiners Report issued Nov. 2008 in Chilean Patent Application No. 1332-2002.

Notice of Allowance issued on Sep. 3, 2010 by the Examiner in U.S. Appl. No. 10/330,360 (U.S. 7,879,831).

Notice of Allowance issued on Jul. 13, 2010 by the Examiner in U.S. Appl. No. 10/330,360 (U.S. 7,879,831).

Decision on Appeal issued on Mar. 16, 2010 by the Board of Patent Appeals and Interferences in U.S. Appl. No. 10/330,360 (US 7,879,831).

Notice of Allowance issued on Sep. 14, 2010 by the Examiner in U.S. Appl. No. 10/330,279 (US 7,846,916).

Notice of Allowance issued on Jul. 13, 2010 by the Examiner in U.S. Appl. No. 10/330,279 (US 7,846,916).

Decision on Appeal issued on Mar. 16, 2010 by the Board of Patent Appeals and Interferences in U.S. Appl. No. 10/330,279 (US 7,846,916).

Notice of Allowance issued on Sep. 16, 2010 by the Examiner in U.S. Appl. No. 10/330,361 (US 7,867,986).

Notice of Allowance issued on Jul. 13, 2010 by the Examiner in U.S. Appl. No. 10/330,361 (US 7,867,986).

Decision on Appeal issued on Mar. 16, 2010 by the Board of Patent Appeals and Interferences in U.S. Appl. No. 10/330,361 (US 7,867,986).

Office Action issued on Oct. 13, 2010 by the Examiner in U.S. Appl. No. 11/979,227 (US 2008/0167365).

Office Action issued on Dec. 22, 2010 by the Examiner in U.S. Appl. No. 11/979,227 (US 2008/0167365).

Notice of Allowance issued on May 27, 2011 by the Examiner in U.S. Appl. No. 11/979,227 (US 2008/0167365).

Stott et al., "Transdermal Drug Delivery From Oestradiol Eutectic Formulations," *Journal of Pharmacy and Pharmacology*, vol. 49, Suppl. 4, p. 82, 1997.

Kaplun-Frischoff et al., "Testosterone Skin Permeation Enhancement by Menthol through Formation of Eutectic with Drug and Interaction with Skin Lipids," *Journal of Pharmaceutical Sciences*, vol. 86, No. 12, pp. 1394-1399, 1997.

Gordon et al., "Modification of phenytoin crystals. II. Infouence of 3-propanoyloxymethyl-5,5-diphenylhydantoin on solution-phase crystallization and related crystal properties," *International Journal of Pharmaceutics*, vol. 79, pp. 171-181, 1992.

Chow et al., "Modification of phenytoin crystals. III. Influence of 3-butanoyloxymethyl-5,5-diphenylhydantioin on solution-phase crystallization and related crystal properties," *International Journal of Pharmaceutics*, vol. 126, pp. 11-19, 1995.

Chow et al., "Modification of phenytoin crystals: influence of 3-acetoxymethyl-5,5-diphenylhydantoin on solution-phase crystallization and related crystal properties," *International Journal of Pharmaceutics*, vol. 75, pp. 219-230, 1991.

De Maury et al., "Etude Des Melanges Binaires Benzoate D'Estradiol-Phenyl Propionate D'Estradiol, Mestranol-Lynestrenol Par Thermomicroscopie Et Analyse Calorimetrique Differentielle," *Thermochimica Acta*, vol. 89, pp. 203-213, 1985.

De Maury et al., "Thermal behaviour of norethisterone acetate and its interaction with ethinylestradiol," *An.. Pharmaceutiques Francaises*, vol. 45, No. 4, pp. 277-288, 1987.

De Maury et al., "Comportement Thermique Et Etude Des Melanges Binaires: Ethinyl-Estradiol-Lynestrenol, Ethinyl-Estradiol-Acetate De Chlormadinone Par Thermomicroscopie, Analyse Calorimetrique Diffrentielle Et Mesure De La Transparence," *Journal of Thermal Analysis*, vol. 32, pp. 121-136, 1987.

\* cited by examiner

ENHANCED DRUG DELIVERY IN TRANSDERMAL SYSTEMS

This application is a continuation of application Ser. No. 10/330,281 filed Dec. 30, 2002, now U.S. Pat. No. 7,456,159 which is a continuation of PCT/US02/16579, filed Jun. 18, 2002, which claims benefit of U.S. application Ser. No. 09/948,107, filed Sep. 7, 2001, and U.S. Provisional Application No. 60/298,381, filed Jun. 18, 2001.

BACKGROUND OF THE INVENTION

1. Field of the Invention

The present invention relates to transdermal drug delivery systems. In particular, the present invention relates to transdermal drug delivery systems for delivering a therapeutically effective amount of a drug that includes a parent drug and a prodrug. The present invention, in particular, relates to transdermal drug delivery systems for delivering steroids, and to methods of making and using the same.

2. Description of the Related Art

The use of a transdermal drug delivery system, for example a pressure-sensitive adhesive containing a drug, as a means for administering therapeutically effective amounts of the medicament is well known. Such known delivery systems involve incorporation of a drug into a carrier such as a polymeric and/or a pressure-sensitive adhesive formulation or other forms of carriers. The pressure-sensitive adhesive must adhere effectively to the skin and permit migration of the drug from the carrier through the skin and into the bloodstream of the patient.

Steroids such as estradiol and norethindrone are especially well known for use in transdermal drug delivery systems, in particular, as hormone replacement therapy. These steroids may be administered singularly, such as the estradiol transdermal drug delivery system sold under the trademark Vivelle7 and Vivelle-Dot 9 manufactured by Noven Pharmaceuticals, Inc. of Miami, Fla. See also U.S. Pat. No. 6,221,383. Alternatively, two or more steroids may be administered together, such as the estradiol/norethindrone acetate transdermal drug delivery system sold under the trademark CombiPatch® also manufactured by Noven Pharmaceuticals. See also U.S. Pat. No. 6,221,383. See also U.S. Pat. No. 5,474,783.

Transdermal drug delivery systems with more than one drug are generally more difficult to formulate in view of different interactions with each drug and the carrier, excipients, etc., even the other drug present. In addition, government agencies that regulate pharmaceutical products, such as the FDA in the United States, require more testing of multiple drugs, individually as well as together to establish efficacy. Thus, when a drug, such as a steroid is administered, it is generally administered in one form only (e.g., norethindrone or norethindrone acetate). See, e.g., U.S. Pat. No. 6,149,935.

The use of a steroid as an additive to act as a crystallization inhibitor in transdermal drug delivery devices where the drug is a hormone is described in WO 99/15156. WO 99/15156 teaches the steroid is present in the device in an amount insufficient to provide significant pharmaceutical or physiological effect. Other patents include U.S. Pat. Nos. 5,633,242; 4,906,169; 5,711,962; 6,153,216; 5,898,032; 5,811,117; and 6,024,974.

One problem in the delivery of drugs, such as steroids from transdermal drug delivery systems lies in the rate of drug release (commonly called "flux" or "permeation rate") from the transdermal system. Specifically, there are many applications in which it would be desirable to have a greater flux of drug (e.g., steroid) from the system. There are also many applications in which it would be desirable to have a decreased flux of drug (e.g., steroid) from the system. In other words, one problem in transdermal drug delivery lies in controlling the transfer of drug from the composition, across the skin and into the subject's bloodstream, thus, controlling the blood profile level of the drug.

One known method for selectively controlling the permeation rate of a drug from a transdermal composition is described in U.S. Pat. No. 5,474,783, assigned to the assignee of the present invention. In this patent, two or more polymers are used in combination to adjust the solubility of the drug in the carrier system. While this method of controlling permeation rate generally works well, it is not always readily possible to control the permeation rate of the drug in the desired manner, such as to achieve a longer or shorter duration of drug delivery and to increase or delay onset of a therapeutic effect.

Another problem in the delivery of drugs, in particular steroids, is the tendency for drugs (e.g., steroids) to crystallize in the carrier of the transdermal system. This results in less steroid being available for transdermal administration. Although the addition of solubilizing agents, such as PVP, help to inhibit crystallization, there are some applications where it is desirable to have a greater crystal inhibiting effect.

U.S. Pat. No. 6,368,616 B1 discloses two phase (aqueous and oily) liquid compositions comprising at least: (A) an NSAID; (B) an alcohol (defined as melt point depressing agent, column 4, line 60); (C) water; and optionally (D) a second melt point depressing agent. The compositions are described as having two phases, with substantially melted solids at 25° C. The "second melt point depressing agents," referred to in the '616 patent are defined as solvents, enhancers, adjuvants or drugs, such as anesthetics or NSAIDs.

U.S. Pat. No. 4,529,601 discloses combination of two different local anesthetic base drugs that melt together at room temperature. Preferred melting points are below 40° C., more preferably, below 25° C.

SUMMARY OF THE INVENTION

One object of the invention is to overcome the disadvantages of the known art described above. Another object of the invention is to provide a transdermal drug delivery system that has increased control over the permeation rate of the drug, onset of effect and/or duration of delivery and/or effect of the drug. Yet another object of the invention is to provide a transdermal drug delivery system that has an improved flux of steroid compared to a system of equal size. Still another object of the invention is to provide a composition that has reduced, or no, crystal formation in the transdermal drug delivery system.

In accomplishing the foregoing and other objects, there has been provided according to one aspect of the present invention a composition, preferably a dermal composition, resulting from an admixture that includes: a therapeutically effective amount of a drug that includes a parent drug and a prodrug; and a pharmaceutically acceptable carrier, wherein the parent drug and prodrug are individually present in an amount sufficient for a pharmacological effect. In a preferred embodiment, the composition has an onset of the therapeutic effect that is longer or shorter than an identical composition having a pharmacologically equivalent amount of the parent drug or prodrug alone. In another preferred embodiment, the composition has a blood level profile that is different from an identical composition having a pharmacologically equivalent amount of the parent drug or prodrug alone. In yet another preferred embodiment, the composition has a permeation rate that is faster or slower than an identical composition having a pharmacologically equivalent amount of the parent drug or prodrug alone. In still another preferred embodiment, the composition has a duration of the therapeutic effect that is longer or shorter than a composition having a pharmacologically equivalent amount of the parent drug alone. In another preferred embodiment, the prodrug is more lipophilic than the parent drug and the prodrug has a greater permeation rate through the skin. In still another preferred embodiment, the melting point of the combined parent drug and prodrug is less than the melting point of either the parent drug or prodrug alone. According to another preferred embodiment, the carrier comprises a pressure-sensitive adhesive that includes two or more polymers, and wherein the permeation of the drug is adjusted by changing the type and/or proportions of the two or more polymers.

According to a preferred aspect of the invention, there has been provided a composition, preferably a dermal composition, resulting from an admixture that includes: a therapeutically effective amount of a pharmaceutically active agent that includes a steroid and a corresponding steroid derivative that provides a source of therapeutically active steroid; and a carrier for the pharmaceutically active agent, wherein the steroid and steroid derivative are present in a weight ratio of 10:1 to 1:10 steroid:steroid derivative. In a preferred embodiment, the steroid derivative is a steroid ester. In another preferred embodiment the carrier is a polymer that includes a pressure-sensitive adhesive.

According to another aspect of the invention, there has been provided a composition for the transdermal delivery of a drug resulting from an admixture that includes: a therapeutically effective amount of a drug that includes an ACE inhibitor and a corresponding ACE inhibitor prodrug; and a pharmaceutically acceptable carrier. Preferably, the ACE inhibitor is ramipril and the prodrug is ramipril methyl and/or ethyl ester.

According to another aspect of the invention, there has been provided a method of making a composition described above that includes forming a mixture of the parent drug and prodrug (preferably a steroid and corresponding steroid derivative) and carrier. Preferably, the carrier is a polymer and the method further includes: forming the blend into a polymer matrix; and drying the polymer matrix to remove volatile solvents to form the composition.

According to another aspect of the invention, there has been provided a method of treating a human or an animal with a therapeutically effective amount of a pharmaceutically active agent, that includes the steps of: applying to the skin of an animal or human being, the composition described above; and maintaining the composition in contact with the skin for a predetermined length of time sufficient to administer the therapeutically amount of the pharmaceutically active agent.

Further objects, features and advantages of the present invention will become apparent from the detailed description of preferred embodiments which follows.

DETAILED DESCRIPTION OF PREFERRED EMBODIMENTS

Figure 1:
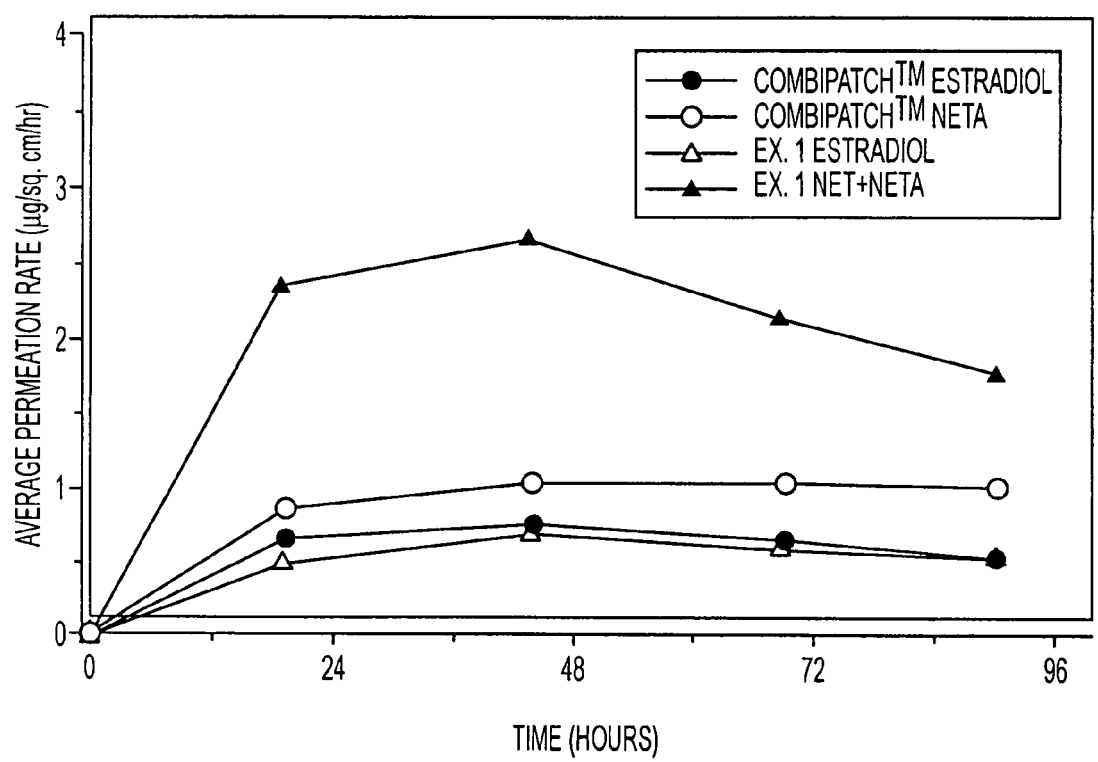
FIG. 1 is a graph illustrating the drug flux from a composition containing norethindrone acetate and estradiol, and a composition containing combined norethindrone/norethindrone acetate and estradiol.

The present invention provides, inter alia, a transdermal drug delivery composition for administration of a therapeutically effective amount of a drug, by delivery of a combined parent drug and prodrug.

A preferred embodiment of the present invention provides, inter alia, a transdermal drug delivery composition for administration of a therapeutically effective amount of a steroid, particularly transdermal compositions having a greater flux than known compositions.

As used herein, "transdermal" delivery is intended both transdermal (or "percutaneous" or "dermal") and transmucosal administration, i.e., delivery by passage of a drug through the skin or mucosal tissue and into the bloodstream.

As used herein, the term, "flux" (also called "permeation rate") is defined as the absorption of the drug through the skin or mucosa, and is described by Fick's first law of diffusion:

$$J = -D(dCm/dx),$$

where J is the flux in $g/cm^2/sec$, D is the diffusion coefficient of the drug through the skin or mucosa in $cm^2/sec$ and $dCm/dx$ is the concentration gradient of the drug across the skin or mucosa.

As used herein, a "drug" is defined as any therapeutically, prophylactically and/or pharmacologically or physiologically beneficial active substance, or mixture thereof, which is delivered to a living organism to produce a desired, usually beneficial, effect. More specifically, any drug which is capable of producing a pharmacological response, localized or systemic, irrespective of whether therapeutic, diagnostic, or prophylactic in nature, in plants or animals is within the contemplation of the invention. The drug may be phamacologically active or may require further biotransformation. The term "drug" encompasses both "parent drug" and "prodrug" as defined below. The drug should be used in amounts sufficient to prevent, cure, diagnose or treat a disease or other condition, as the case may be.

As used herein, a "parent drug" is defined the same as a "drug," except that it does not undergo biotransformation to render it more pharmacologically active.

As used herein, a "prodrug" is defined as a pharmacologically less active derivative of a parent drug molecule that requires biotransformation, either spontaneous or enzymatic, within the organism to release the more active parent drug. Prodrugs are variations or derivatives of the parent drugs which have groups cleavable under metabolic conditions. Prodrugs become the parent drugs which are pharmaceutically active in vivo, when they undergo solvolysis under physiological conditions or undergo enzymatic degradation. Prodrugs may be called single, double, triple, etc., depending on the number of biotransformation steps required to release the active parent drug within the organism, and indicating the number of functionalities present in a precursor-type form. Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. See, Bundgard, Design of Prodrugs, pp. 7-9, 21-24, Elsevier, Amsterdam 1985; Silverman, The Organic Chemistry of Drug Design and Drug Action, pp. 352-401, Academic Press, San Diego, Calif., 1992; and Burger's Medicinal Chemistry and Drug Chemistry, Fifth Ed., Vol. 1, pp. 172-178, 949-982 (1995).

As used herein, "pharmacologically equivalent amount" is defined as an amount of the parent drug or prodrug that has an equivalent therapeutic effect as a selected combined amount of the parent drug and prodrug.

As used herein "blood profile level" is defined as the concentration in blood level of the parent drug or prodrug over a selected period of time, usually from beginning of administration.

As used herein, a steroid is defined as a family of lipid compounds that includes the sterols, bile acids, cardiac glycosides, saponins, corticoid steroids and hormones. The basic structure of the steroid is a well known 4 ring fused structure.

According to one aspect of the invention, the inventor has found that the permeation rate of the blood profile level of a subject being administered a drug transdermally can be more readily controlled by the use of a prodrug in combination with the parent drug. By administering a parent drug and prodrug combination, the blood profile level can be affected by two significant aspects: (1) overall solubility of the parent drug/prodrug in the carrier; and (2) selection of the prodrug to affect its transport through the skin and metabolism into the parent drug in the body of the subject.

By controlling the overall solubility of the parent drug/prodrug within the carrier, the overall saturation concentration of the parent drug/prodrug, and hence the rate of release of the drug from the carrier will be increased and/or decreased. The overall solubility of the parent drug/prodrug in the carrier can be controlled by adjusting the concentration of the parent drug and prodrug relative to each other. This method relies upon the different solubilities that the parent drug and prodrug will have in the composition, due to the different polarity of the parent drug and prodrug and other factors such as hydrogen bonding. Changes in substituents on the molecule can significantly effect the solubility. Also, the use of co-solvents and other solubilizing agents can be used to adjust the solubilities of the parent drug and prodrug in the composition.

Another related method for controlling the overall solubility of the parent drug/prodrug concentration is to use a solubility based selection of the polymers that make up the carrier. A solubility based selection of polymers to optimize the permeation rate of a parent drug or prodrug without its prodrug or parent drug is described in the '783 patent described above, which is incorporated by reference in its entirety. The same principles regarding the solubility of a drug in a polymer blend will also apply to a carrier with a parent drug/prodrug combination.

The term "blend" is used herein to mean that there is no, or substantially no, chemical reaction or cross-linking (other than simple H-bonding) between the polymers in the polymer adhesive carrier.

The polymers comprising the multiple polymer adhesive carrier are inert to the drug, and are preferably immiscible with each other. Forming a blend of multiple polymers results in an adhesive carrier having a characteristic "net solubility parameter," the selection of which advantageously permits a selectable modulation of the delivery rate of the drug by adjusting the solubility of the drug in the multiple polymer adhesive carrier.

Solubility parameter, also referred to herein as "SP", has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," J. Soc. Cosmet. Chem., Vol. 36, pages 319-333 (1985). Many methods have been developed for the determination of solubility parameters, ranging from theoretical calculations to totally empirical correlations. The most convenient method is Hildebrand's method, which computes the solubility parameter from molecular weight, boiling point and density data, which are commonly available for many materials and which yields values which are usually within the range of other methods of calculation:

$$SP=(\Delta Ev/V)^{1/2},$$

where V=molecular weight/density and $\Delta E_V$=energy of vaporization.

Alternatively written, $SP=(\Delta H_V/V-RT/V)^{1/2}$
where $\Delta H_V$=heat of vaporization, R=gas constant, and T is the absolute temperature, °K. For materials, such as high molecular weight polymers, which have vapor pressures too low to detect, and thus for which $\Delta H_V$ is not available, several methods have been developed which use the summation of atomic and group contributions to $\Delta H_V$:

$$\Delta H_V = \Sigma_i \Delta h_i,$$

where $\Delta h_i$ is the contribution of the ith atom or group to the molar heat of vaporization. One convenient method has been proposed by R. F. Fedors, Polymer Engineering and Science, Vol. 14, p. 147 (1974). In this method $\Delta E_V$ and V are be obtained by simply assuming that
$\Delta E_V = \Sigma_i \Delta e_i$ and $V = \Sigma_i v_i$ where $\Delta E_i$ and $v_i$ are the additive atomic and group contributions for the energy of vaporization and molar volume, respectively.

Yet another method of calculating the solubility parameter of a material is described by Small, J. Applied Chem. Vol. 3, p. 71 (1953).

Solubility parameters of some exemplary adhesive polymers are set forth in the '783 patent.

The transdermal permeation rate of the parent drug/prodrug combination is controlled by varying the polymer components of the polymer adhesive carrier so as to alter the difference in the solubility parameter of the multiple polymer adhesive carrier relative to that of the parent drug/prodrug combination.

The transdermal permeation rate can also be controlled by varying the relative proportions of the polymers comprising the polymer adhesive carrier.

The polymer adhesive carrier is preferably formulated so that it is a pressure-sensitive adhesive at room temperature and has other desirable characteristics for adhesives used in the transdermal drug delivery art; such characteristics include good adherence to skin, ability to be peeled or otherwise removed without substantial trauma to the skin, retention of tack with aging, etc. In general, the multiple polymer adhesive carrier should have a glass transition temperature (Tg), measured using a differential scanning calorimeter, of between about −70° C. and 0° C.

Selection of the particular polymer composition is governed in large part by the parent drug/prodrug to be incorporated in the device, as well as the desired rate of delivery of the parent drug/prodrug. Those skilled in the art can readily determine the rate of delivery of drugs from the polymer transdermal adhesive carrier in order to select suitable combinations of polymers and drug for a particular application. Various techniques can be used to determine the rate of delivery of the drug from the polymer. Illustratively, the rate of delivery can be determined by measuring the transfer of drug from one chamber to another through cadaver skin over time, and calculating, from the obtained data, the drug delivery or flux rate. Specific polymers, such as preferred acrylic-based and silicone-based polymers, are described below.

The other method for controlling the blood plasma profile of subject is in the selection of the prodrug, such as based on its molecular weight or polarity. By increasing the molecular weight of the prodrug, the time to the onset of permeation of effective amounts of the prodrug will increase relatives to the parent drug. One example of this effect is in the use of norethindrone and norethindrone acetate. The permeation rate of norethindrone rapidly peaks after application, whereas norethindrone acetate having a higher molecular weight reaches a maximum after the norethindrone permeation rate begins to decline. See, e.g., FIG. 2.

In a related fashion, as the molecular weight of the prodrug increases, the permeation rate of the prodrug will be slower than the parent drug. Consequently, increasing the concentrations of higher molecular weight prodrugs can be used to offset decreasing permeation rates of parent drugs where continued drug delivery over time is desired.

Of course, it should be understood that there is a certain degree of interrelationship between the two broad concepts described above. For example, molecular weight will affect both the amount of prodrug that can solubilized in the carrier as well as its transport through the skin.

Another parent drug/prodrug combination method to control the blood profile level is by the selection of a prodrug based on its different polarity. As explained in copending application Ser. No. 10/014,785, it is believed that the more lipophilic prodrug facilitates the entry of the prodrug into the stratum corneum of the intact skin of a subject where it is ultimately hydrolyzed into the pharmacologically active and more polar parent drug. The hydrolysis of the blocked functional group in the prodrug to the functional groups in the parent drug, in turn, accelerates the diffusion of the drug through the skin and into the blood of the subject. That is, the more lipophilic prodrug is initially drawn into the lipophilic stratum corneum at a rate faster than the corresponding parent drug. During transport through the skin, the prodrug is at least partially hydrolyzed back into the parent drug. As hydrolysis takes place, the more polar parent drug is expelled from the lipophilic skin into the relatively polar blood stream. Thus, by selecting the prodrug based on its polarity, the permeation rate across the skin can be controllably increased relative to the corresponding parent drug. Thus, by using a prodrug in addition to the parent drug, the composition will provide a faster permeation rate and onset.

Also, the onset and duration may be also controlled by the use of prodrugs, due to the fact that systemic metabolism of the parent drug may be reduced by the use of prodrugs. See generally, Bundgaard. That is, selection of appropriate prodrug allows even greater duration of effective therapy when in-vivo conversion rates to the active parent drug entity are concerned. Initial dose can be introduced as the active parent drug entity while concomitant administration of a long-acting prodrug occurs. The long-acting prodrug will be metabolized, e.g., over the course of days to weeks to maintain therapeutic levels of active parent drug. Examples of commercially available long-acting esters are haloperidol decanoate (Haldol®) and testosterone enanthate (Delatestryl®). Parenteral administration of these molecules result in therapeutic levels of parent drug being sustained for 2-4 weeks. A similar long acting effect would be expected in transdermal drug delivery.

The inventor has also found that the inventive combination of a parent drug and prodrug can effect the melting point and hence the crystallization of the parent drug/prodrug combination in the carrier. The quantity of drug loading possible, without crystallization, in transdermal platforms is dictated by many factors. Among these are drug functionality (acidic, basic), drug polarity or lack of polarity, solvents, matrix polymers and other excipient selections. Typically, the solvents, polymers and excipients are used in a plethora of combinations to optimize transdermal drug delivery for a given drug.

Figure 5:
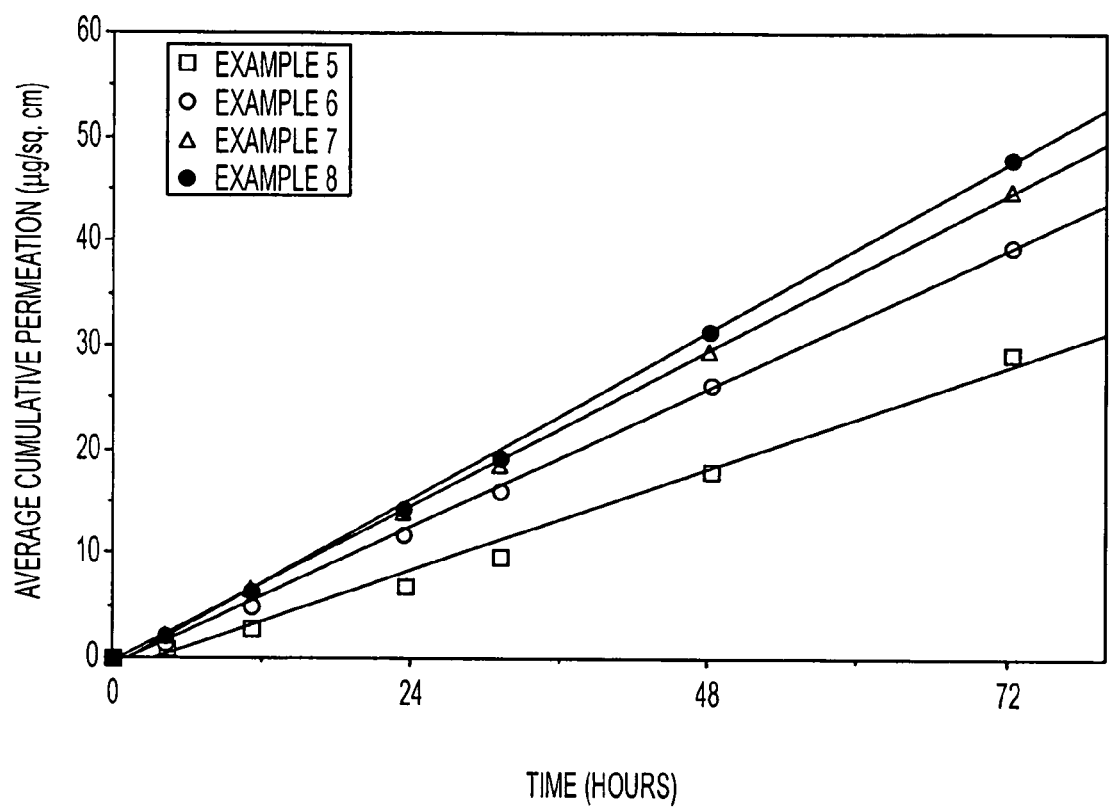
FIG. 5 shows cumulative permeation for norethindrone for various combinations of parent drug/prodrug.
Figure 6:
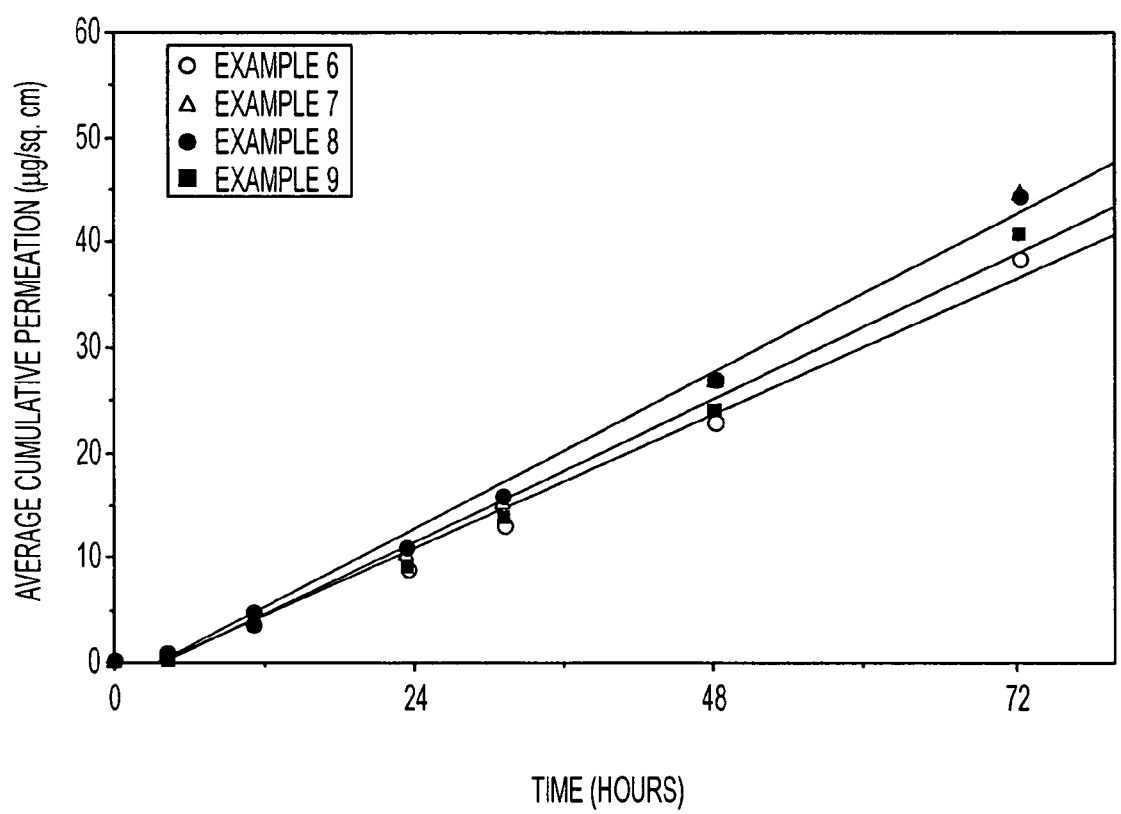
FIG. 6 shows cumulative permeation for norethindrone acetate for various combinations of parent drug/prodrug.

The melting point of a pure drug is constant at STP and must be consistent lot to lot to be pharmaceutically acceptable as a raw material. The inventor has found a pharmaceutically acceptable way of reducing the purity (and thereby the melting point) of a given drug while still maintaining a pharmacologically equivalent effect, by utilizing the parent drug/prodrug combination. The two compounds interact to produce a mixture that exhibits a lower initial melting point than either individual compound. This lower melting point parent drug/prodrug combination results in substantial permeation rate enhancement when properly incorporated into transdermal platforms. This enhancement is due primarily to increased non-crystallized drug loading possible with these blends. Observations show (a) increased drug flux with the parent drug/prodrug mixtures flux over each individually (FIG. 7) and (b) increased permeation of parent drug is achieved by increasing prodrug loading (FIGS. 5 and 6).

Use of a prodrug for enhancement of drug permeation is preferred to incorporating small molecule enhancers such as ethanol, polyhydric alcohols or terpenes because such prodrugs also contribute to achieving delivery of a therapeutically effective dose. Moreover, use of prodrugs rather than small molecule enhancers can reduce or eliminate irritation, stability and processing issues associated with such enhancers when making a transdermal system.

The melting point depression for various combinations of norethindrone and norethindrone acetate and estradiol and an estradiol prodrug are shown in Tables I and II. The indicated amounts of parent drug and prodrug were mixed by sieving the crystal powder drugs through a 250 micron screen. A sample of each mixture was placed in a capillary tube and melting point measurements were performed according to USP Reference Standards using a Haake melting point apparatus. All ratios demonstrate depressed melting points when compared to samples of the individual compounds although optimal depression of melt point ranges is observed when the amount of prodrug exceeds the parent drug.

TABLE I

Melting Point Ranges

| Norethindrone | Norethindrone Acetate | Initial Melting Point ° C. | Final Melting Point ° C. |
|---|---|---|---|
| 40 mg | 40 mg | 146 | 183 |
| 20 mg | 40 mg | 147 | 174 |
| 20 mg | 60 mg | 146 | 171 |
| 20 mg | 80 mg | 146 | 155 |
| 10 mg | 90 mg | 147 | 154 |
| 40 mg | 20 mg | 147 | 191 |
| 80 mg | 20 mg | 148 | 197 |
| 90 mg | 10 mg | 152 | 202 |
| 50 mg | 0 mg | 206 | 209 |
| 0 mg | 50 mg | 163 | 166 |

Similar testing was performed with estradiol and some of its corresponding prodrug at a 1:1 ratio. The results, shown in Table II, also demonstrate a depressed melting point range. Utilizing a low melting point estradiol prodrug appears to be best at lowering estradiol's melting point.

TABLE II

| Compound | Melting Point Range ° C. |
|---|---|
| Estradiol | 177 |
| Estradiol 17-enanthate | 94-95 |
| Estradiol 17-acetate | 220-222 |
| Estradiol: estradiol 17-enanthate | 88-129 |
| Estradiol: estradiol 17-acetate | 162-200 |

It appears that a melting point depression is achieved by combining a parent drug and a prodrug, and this phenomenon likely accounts for crystal inhibition in such transdermal combination platforms. Examining melt point interactions of two or more combined drug entities provides an improved method of predicting and achieving drug crystal inhibition. Melt point interactions are also a simpler methodology than solubility parameter crystallization observations since solubility parameter determining factors are far more numerous and often somewhat more difficult to define. Accordingly, melt point depression measurements will provide another tool by which desirable drug combinations can be determined, and subsequently tested for skin permeation performance in suitable matrix platforms.

Prodrugs that would be most useful are those that lower the parent drug/prodrug combination's melting point the greatest. Parent drug/prodrug combinations that exhibited higher melting points (than the lowest melting point individually) would be particularly useful in controlling permeation rates which were otherwise too high or fast, or exhibited drug depletion prior to the end of the desired time period.

This becomes particularly important in formulating the next generation of transdermal drug delivery systems (particularly for hormone replacement therapy) that will be required to deliver a therapeutically effective amount of a drug over the course of up to one week or more. To achieve an extended delivery, increasing drug concentration is typically required but in turn increases problems of crystallization. Determining the melting point of parent drug/prodrug combinations will provide a method and a means of optimizing and controlling permeation rates.

Results of melting point effects on crystalline drug combination (i.e., parent and prodrugs) suggest that preferred embodiments of this invention will utilize prodrugs with lower melting points than the parent drug.

Particularly useful drug combinations include steroids and their corresponding prodrugs, such as those steroids described herein. It has been found that estradiol enanthate and estradiol propionate are preferred in combination with estradiol versus estradiol acetate. With testosterone, testosterone enanthate is preferred over testosterone proprionate. Other useful drugs include ACE inhibitors and their prodrugs, such as ramipril and its prodrugs, particularly ramipril methyl ester and ramipril ethyl ester. For the general invention, the weight ratio of the parent drug:prodrug is preferably 10:1 to 1:10. A more preferred ratio is 6:1 to 1:6 and more preferably 1:3 to 3:1.

In a particularly preferred aspect of the invention, the parent drug is ramipril and the prodrug is ramipril methyl ester and/or ramipril ethyl ester. Consistent with the present invention, applicants have found that the use of ramipril together with one of its prodrugs, in this case the methyl or ethyl ester, has been found to provide a modified flux (in this case an increased flux) over the parent drug or prodrug alone. The use of the methyl ester with the parent drug ramipril is preferred since it provides a greater flux than the ethyl ester. The preferred weight ratio for ramipril:ramipril methyl ester is generally 2:1 to 1:9. The preferred weight ratio for ramipril: ramipril ethyl ester is generally 1:1 to 1:5, more preferably 1.1:1 to 1.1:5.

In a particularly preferred aspect of the invention, the parent drug is a steroid and the prodrug is a corresponding steroid derivative. Useful for this aspect of the invention are steroids having a free hydroxy group at a position on the steroid ring, such as the 17-position, the 3-position, or at the 11-position on the fused ring. Particularly preferred are hormones such as estrogens, progestins, and androgens. The corresponding steroid prodrug (in this embodiment called steroid derivative) is defined as a corresponding structure to the steroid where the free hydroxy at the 3, 11 or 17 position has been reacted with an alcohol reactive moiety. Particularly preferred are steroid derivatives reacted at the 17 position. Regardless of whether the steroid or the corresponding steroid derivative is incorporated in the carrier composition as the dominant drug, each provides a source of steroid in the bloodstream to achieve the intended physiological effect which, in the case of the corresponding steroid derivative, occurs through metabolic conversion of the derivative.

A steroid ester is the corresponding structure to the steroid where the free hydroxy group on the ring has been esterified. Examples of a steroid and its corresponding ester include estradiol and estradiol benzoate, estradiol 17-beta cypionate, estradiol 17 propionate, estradiol hemisuccinate (eutocol), estradiol enanthate, estradiol undecylate estradiol acetate, and estradiol propionate, etc. Another example is testosterone and its corresponding ester of testosterone such as 17 beta-cypionate, testosterone enanthate, testosterone nicotinate, testosterone phenylacetate, testosterone propionate, etc. Also included are non-esters that have groups on the 17 position such as testosterone 17-chloral hemiacetal, or ethers that have groups on the 3-position such as estradiol 3-methyl ether.

Other steroids that can be used include progestins such as allylestrenol, anagestone, desogestrel, dimethisterone, dydrogesterone, ethisterone, ethynodiol, gestodene, haloprogesterone, 17-hydroxy-16-methylene-progesterone, 17.alpha.-hydroxyprogesterone, lynestrenol, medroxyprogesterone, melengestrol, norethindrone, norethynodrel, norgesterone, norgestimate, norgestrel, norgestrienone, norvinisterone, pentagestrone, and trimigestone.

Anabolic steroids can include androisoxazole, androstenediol, bolandiol, bolasterone, clostebol, ethylestrenol. formyldienolone, 4-hydroxy-19-nortestosterone, methandriol, methenolone, methyltrienolone, nandrolone, norbolethone, oxymesterone, stenbolone and trenbolone. Androgenic steroids can include boldenone, fluoxymesterone, mestanolone, mesterolone, methandrostenolone, 17-methyltestosterone, 17.alpha.-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal and tiomesterone.

Estrogens can include conjugated estrogenic hormones, equilenin, equilin, estradiol, estradiol benzoate, estradiol 17.beta.-cypionate, estriol, estrone, ethinyl estradiol and mixtures thereof.

Further steroids can include glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone, Fluprednidene, Fluprednisolone, Flurandrenolide, Formocortal, Halcinonide, Halometasone, Halopredone, Hydrocortamate, Hydrocortisone, Mazipredone, Medrysone, Meprednisone, Methyolprednisolone, Mometasone Furoate, Paramethasone, Prednicarbate, Prednisolone, Prednisone, Prednival, Prednylidene, Tixocortal, and Triamcinolone, Also included are mineralocorticoids such as Aldosterone, Deoxycorticosterone and Fludrocortisone.

In typical known devices the corresponding steroid derivative is administered in view of crystallizations problems that occur with the use of the non-derivative steroid. The present inventors have discovered that when the steroid is administered together with its corresponding steroid derivative, a synergism in flux is observed as well as a reduction in crystallization. That is, the flux from the combination of steroid and steroid derivative is greater than the flux of an equal amount of steroid or steroid derivative alone. For example, in a system that contains estradiol and norethindrone acetate, the addition of norethindrone and a reduction in the amount of norethindrone acetate such that the combined amount equals the original amount of norethindrone acetate results in increased delivery of norethindrone/norethindrone acetate.

Another unexpected advantage of the present invention is that the total amount of steroid/corresponding steroid derivative delivered from the system is significantly greater than the amount drug from a composition containing the steroid or corresponding steroid derivative alone. For example, applicants have found that for compositions containing both norethindrone acetate and norethindrone, the total amount of steroid delivered from the system was 65% greater than a system containing a comparable amount of norethindrone acetate alone.

In order to achieve this synergistic effect, the weight ratio of steroid/corresponding steroid derivative is important. The ratio is preferably in the range of 10:1 to 1:10 steroid:corresponding steroid derivative. A more preferred ratio is in the range of 6:1 to 1:6 steroid:corresponding steroid derivative. The ratios providing the greatest synergism depend on the pharmaceutically active agents in the system. For example, for the administration of the corresponding steroid and steroid derivative alone, a greater amount of steroid relative to corresponding steroid derivative produces the greatest synergy. In this embodiment, a preferred ratio is 1:1 to 3:1, more preferably 3:2 to 5:2, even more preferably about 2:1. However, when an additional steroid is present (such as estradiol) the opposite ratio gives the greatest synergy. In this embodiment, a preferred ratio is 1:1 to 1:3, more preferably 2:3 to 2:5, even more preferably 1:2 steroid:corresponding steroid derivative. Any ratio that provides a synergistic flux is within the scope of the present invention.

Moreover, it further has been found that combinations of steroid derivatives also result in inhibiting crystallization of the drug species in the transdermal carrier compositions, with certain derivatives again working better than others. As shown in Table III, the addition of estradiol methyl ether to estradiol acetate in a transdermal carrier composition significantly improves crystal inhibition, whereas the combination of estradiol acetate and estradiol propionate shows no improvement, at the concentrations tested. The examples were observed through a microscope for crystal formation after two weeks maintained at 25° C. and a relative humidity of 65% to 70%, using a viewing field of 38.5 mm$^2$.

TABLE III

| % INGREDIENT | EXAMPLE A | EXAMPLE B | EXAMPLE C | EXAMPLE D | EXAMPLE E |
|---|---|---|---|---|---|
| Estradiol acetate | 3 | — | — | 3 | 3 |
| Estradiol propionate | — | 3 | — | 3 | — |
| Estradiol methyl ether | — | — | 3 | — | 3 |
| Acrylic Adhesive (GMS 788) | 5 | 5 | 5 | 5 | 5 |
| Oleyl Alcohol | 6 | 6 | 6 | 6 | 6 |
| Dipropylene Glycol | 9 | 9 | 9 | 9 | 9 |
| Silicone Adhesive (BIO-PSA 7-4603) | 75 | 75 | 75 | 72 | 72 |
| Polyvinylpyrrolidone (KOLLIDON-30) | 2 | 2 | 2 | 2 | 2 |
| CRYSTAL FORMATION | ≧100 | Long branched crystals throughout | None | Branched crystals throughout | ≦2 |

Determining which steroid derivatives work better than others in combination with steroids or other steroid derivatives can be determined through routine experimentation using the present specification as a guide.

The following description is described with respect to parent drugs/prodrugs generally, but applies equally to the preferred embodiment of steroid/steroid derivatives described above.

The combined amount of parent drug/prodrug present in the composition can vary broadly and depends on many factors such as the carrier, the length of administration, desired therapeutic effect, etc. The minimum amount of parent drug/prodrug in the system is selected based on the amount of parent drug/prodrug which passes through the skin in the time span for which the composition is to provide therapy. Normally, the amount of parent drug/prodrug in the composition can vary from about 0.1% to about 50% by weight, and preferably, for the lower steroid/corresponding steroid derivative doses permitted by this invention, from about 0.3% to about 20%. Other possible ranges can include 0.1% to 10%, or 0.1% to 6% by weight.

The drug is present in a carrier. "Carrier" or "vehicle" as used herein refers to carrier materials suitable for transdermal drug administration, and include any such materials known in the art, e.g., any liquid, gel, solvent, liquid diluent, solubilizer, polymer or the like, which is nontoxic and which does not significantly interact with other components of the composition or the skin in a deleterious manner. The carrier is present in an amount sufficient to achieve its function of carrying the parent drug/prodrug. Preferably, the carrier is present in an amount ranging from 2 to 99 wt %, more preferably 30 to 90 wt %, even more preferably 40 to 80 wt %. The carrier is preferably substantially free of water and more preferably contains no water.

Particularly preferred carriers are flexible, finite compositions. The phrase "flexible, finite system" is intended to mean a solid form capable of conforming to the surface with which it comes into contact, and which is capable of maintaining the contact in such solid form so as to facilitate topical application without adverse physiological response, and without being appreciably decomposed by aqueous contact during administration to a patient. Particularly preferred flexible, finite systems are polymer carriers such as pressure-sensitive adhesive matrix type in which the parent drug/prodrug is dispersed directly in the pressure-sensitive adhesive or reservoir type carriers.

Illustrative examples of suitable adhesives as matrix type flexible, finite delivery systems include those described in U.S. Pat. Nos. 5,474,783, and 5,656,386 both assigned to Noven Pharmaceuticals, Inc., Miami, Fla. (incorporated herein by reference in their entireties). Other flexible, finite systems known in the art include films, plasters, dressings, and bandages, as well as multilayer delivery systems in which the parent drug/prodrug is solubilized or contained in one or more separate layers and reservoir-type delivery systems in which the parent drug/prodrug is solubilized or contained in a reservoir or depot separate from the adhesive which attaches directly to the skin or mucosa.

As noted above, particularly preferred carriers are pressure-sensitive adhesive flexible, finite carriers. These can include any viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB), of different molecular weights, wherein each resultant mixture is pressure-sensitive. Other useful rubber based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof.

Other useful pressure-sensitive adhesives ("PSA") can include acrylic-based pressure-sensitive adhesives and silicone-based pressure-sensitive adhesives as described in U.S. Pat. Nos. 5,474,783, and 5,656,386. Suitable commercially available acrylic-based polymers can include adhesives are commercially available and include the polyacrylate adhesives sold under the trademarks Duro-Tak by National Starch and Chemical Corporation, Bridgewater, N.J., such as Duro-Tak 87-2194, Duro-Tak 87-2196, Duro-Tak 87-1197, 87-4194, 87-2510, 87-2097 and 87-2852. Other suitable acrylic-based adhesives are those sold under the trademarks Gelva-Multipolymer Solution (GMS) (Monsanto; St. Louis, Mo.), such as GMS 737, 788, 1151, 3087 and 7882.

Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989), incorporated by reference in its entirety. Other useful silicone-based pressure sensitive adhesives are described in the following U.S. Pat. Nos. 4,591,622; 4,584,355; 4,585,836; and 4,655,767. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich.

The amount of the polymer carrier can range from 2 to 99 wt %, preferably, 30 to 90 wt %, even more preferably 40 to 80 wt %.

The pressure-sensitive adhesives can be blended to modulate the solubility of the drug in the carrier system such as described in the '783 patent. In a particularly preferred embodiment of the invention, the multiple polymer adhesive system comprises a pressure-sensitive adhesive blend of an acrylic-based polymer, a silicone-based polymer, and a soluble PVP (described below). The acrylic-based polymer and silicone-based polymer are preferably in a ratio by weight, respectively, from about 2:98 to about 96:4, more preferably from about 2:98 to about 90:10, and even more preferably about 2:98 to about 86:14. The amount of acrylic-based (also referred to broadly as a polyacrylate) polymer and silicone-based polymer (also referred to broadly as a polysiloxane) is adjusted so as to modify the saturation concentration of the parent drug/prodrug in the ternary multiple polymer adhesive system in order to affect the rate of delivery of the parent drug/prodrug from the system and through the skin. Other useful ranges include about 5-85% by weight of the acrylate-based polymer, 10-90% by weight of polyisobutylene and 5-95% by weight of silicone-based polymer.

The transdermal drug delivery system can also contain agents known to accelerate the delivery of the parent drug/prodrug through the skin. These agents have been referred to as skin-penetration enhancers, accelerants, adjuvants, and sorption promoters, and are collectively referred to herein as "enhancers" and are described in U.S. Pat. No. 6,221,383. They can include polyhydric alcohols such as dipropylene glycol, propylene glycol, and polyethylene glycol which enhance parent drug/prodrug solubility; oils such as olive oil, squalene, and lanolin; fatty ethers such as cetyl ether and oleyl ether; fatty acid esters such as isopropyl myristate which enhance parent drug/prodrug diffusibility; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate. Particularly preferred are combinations of polyhydric alcohols such as glycerine, dipropylene glycol, butylene glycol, propylene glycol and one or more of oleyl alcohol and oleic acid.

In some embodiments, the invention can also include a plasticizer or tackifying agent is incorporated into the formulation to improve the adhesive characteristics of the pressure-sensitive adhesive composition. Such plasticizers or tackifying agents include: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins.

The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent.

For parent drug/prodrug molecules which are not readily soluble in the polymer system, a co-solvent for the parent drug/prodrug and polymer can be added. Co-solvents, such as lecithin, retinal derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the parent drug/prodrug in the multiple polymer adhesive system.

In addition to the use of the parent drug/prodrug combinations to inhibit crystallization, other crystallization inhibiting agents can be used. One known agent is polyvinylpyrrolidone (PVP), preferably soluble PVP as described in detail in U.S. Pat. No. 6,221,383. The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. The PVP usable with the present invention, preferably has a molecular weight of about 2,000 to 1,100,000, more preferably 5,000 to 100,000, and most preferably 7,000 to 54,000.

The amount and type of PVP required in the foregoing preferred embodiment will depend on the quantity and type of parent drug/prodrug present in the adhesive, as well as the type of adhesive, but can be readily determined through routine experimentation. Typically, the PVP is present in an amount from about 1% to about 20% by weight, preferably from about 3% to about 15% by weight. However, the amount of PVP can be higher than 20% for example, up to 40%, depending on the particular parent drug/prodrug used and on the desired properties of the blend. One commercially useful PVP is sold under "Kollidon," such as "Kollidon 10," "Kollidon 17 PF," "Kollidon 25," "Kollidon 90," "Kollidon 30," and "VA 64" a trademark of BASF AG, Ludwigshafen, Germany. Another useful PVP is sold under Kollidon CL-M also a trademark of BASF AG.

The compositions of this invention may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of parent drug/prodrug delivery. Suitable clays include aluminum silicate clay, kaolinite, montmorillonite, atapulgite, illite, bentonite, halloysite and the like.

A device, or individual dosage unit, of the present invention can be produced in any manner known to those of skill in the art. After the dermal composition is formed, it may be brought into contact with the backing layer in any manner known to those of skill in the art. Such techniques include calender coating, hot melt coating, solution coating, etc. Of course, backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Dow Corning Corporation designated Bio-Release7. liner and Syl-off7 7610 liner. For preferred embodiments in which a polysiloxane is part of the multiple polymeric adhesive carrier, the release liner must be compatible with the silicone adhesive. An example of a suitable commercially available liner is 3M's 1022 Scotch Pak.7 The configuration of the transdermal delivery system of the present invention can be in any shape or size as is necessary or desirable. Illustratively, a single dosage unit may have a surface area in the range of 1 to 200 $cm^2$. Preferred sizes are from 5 to 60 $cm^2$.

In a preferred method aspect of the invention where the carrier is a flexible, finite polymer, one or more polymers are blended, optionally with PVP to result in a pressure-sensitive adhesive composition, or transdermal drug delivery system adhesive system (with incorporated parent drug:prodrug), which controls delivery of an incorporated parent drug:prodrug and through the epidermis. In a preferred embodiment of the invention, a transdermal drug delivery system is prepared by mixing a soluble PVP, polyacrylate, polysiloxane, parent drug/prodrug, optional enhancer(s), co-solvent(s), and tackifying agents, if needed, in an appropriate volatile solvent(s), then casting the mixture and removing the solvent(s) by evaporation to form a film. Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

An exemplary general method for the preparation of an embodiment is as follows:

1. Appropriate amounts of solvent(s), optional enhancer(s), optional PVP and organic solvent(s) (for example toluene) are combined and thoroughly mixed together in a vessel.

2. The parent drug:prodrug is then added to the mixture and agitation is carried out until the parent drug/prodrug is uniformly mixed in.

3. Appropriate amounts of polymer are then added to the parent drug/prodrug mixture, and thoroughly mixed.

4. The formulation is then transferred to a coating operation where it is coated onto a protective release liner at a controlled specified thickness. The coated product is then passed through an oven in order to drive off all volatile processing solvents.

5. The dried product on the release liner is then joined to the backing material and wound into rolls for storage.

6. Appropriate size and shape "systems" are die-cut from the roll material and then pouched.

The order of steps, the amount of the ingredients, and the amount and time of agitation or mixing may be importance process variables which will depend on the specific polymers, parent drug/prodrug, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 square centimeters is contemplated, and the presently preferred sizes are: 5, 10, 15, 20, 30, 40, and 60 are centimeters.

EXAMPLES

The following specific examples are included as illustrative of transdermal delivery systems and compositions within the contemplation of the invention. These examples are in no way intended to be limiting of the scope of the invention. The weights percentages in the examples are based on dry weight of the system, unless other noted. In the figures, "NET" stands for norethindrone, and "NETA" stands for norethindrone acetate.

The following commercially available adhesives were used in the examples: "Duro-Tak 87-2287" is a trademark of NATIONAL STARCH AND CHEMICAL CORPORATION, Bridgewater, N.J. for polyacrylate adhesives in organic solutions.

"Bio-PSA 7-4603" is a trademark of DOW CORNING CORPORATION, MEDICAL PRODUCTS, Midland, Mich. for polysiloxane adhesives in organic solutions.

"Gelva-Multipolymer Solution (GMS) 737 and 788" are trademarks of the Monsanto Company, Saint Louis, Mo. for polyacrylate adhesives in organic solution.

"KOLLIDON 30 and VA 64" are trademarks of BASF Aktiengesellschaft, Ludwigschaften, Germany for polyvinylpyrrolidone polymers and the vinyl acetate/vinylpyrrolidone copolymer.

Example 1 and Comparative Example 1

A transdermal delivery composition was prepared with the following ingredients:

| | |
|---|---|
| Norethindrone | 1.2% |
| Estradiol | 0.9 |
| Norethindrone Acetate | 2.5 |
| PVP/VA Copolymer (VA64) | 15.0 |
| Acrylic PSA (GMS737) | 5.0 |
| Oleic Acid | 3.0 |
| Dipropylene Glycol | 9.0 |
| Silicone PSA (7-4603) | 63.4 |

Flux of the steroids through the cadaver skin in vitro from the formulation of Example 1 is shown in FIG. 1 as triangles (Δ and ▲). Also shown as a comparative example ("CE") is the flux for the commercially available CombiPatch 9 product that contains only estradiol and norethindrone acetate, which are shown as circles (O or ●). As FIG. 1 indicates, the flux for the combined norethindrone/norethindrone acetate of Example 1 was significantly higher than norethindrone acetate alone of the CombiPatch 9 product, while the flux of estradiol was unaffected. The flux of estradiol was approximately the same.

Example 2 and Comparative Examples (CE) 2

Transdermal steroid/corresponding steroid derivative delivery compositions were prepared with the following ingredients:

| Formulation | CE 2-1 | CE 2-2 | Ex. 2 |
|---|---|---|---|
| Norethindrone | 1.2% | 0% | 1.2% |
| Estradiol | 0.9 | 0.9 | 0.9 |
| Norethindrone Acetate | 0 | 2.5 | 2.5 |
| PVP/VA Copolymer (VA64) | 15.0 | 15.0 | 15.0 |
| Acrylic PSA (GMS737) | 5.0 | 5.0 | 5.0 |
| Oleic Acid | 3.0 | 3.0 | 3.0 |
| Dipropylene Glycol | 9.0 | 9.0 | 9.0 |
| Silicone PSA (7-4603) | 65.9 | 64.6 | 63.4 |

Figure 2:
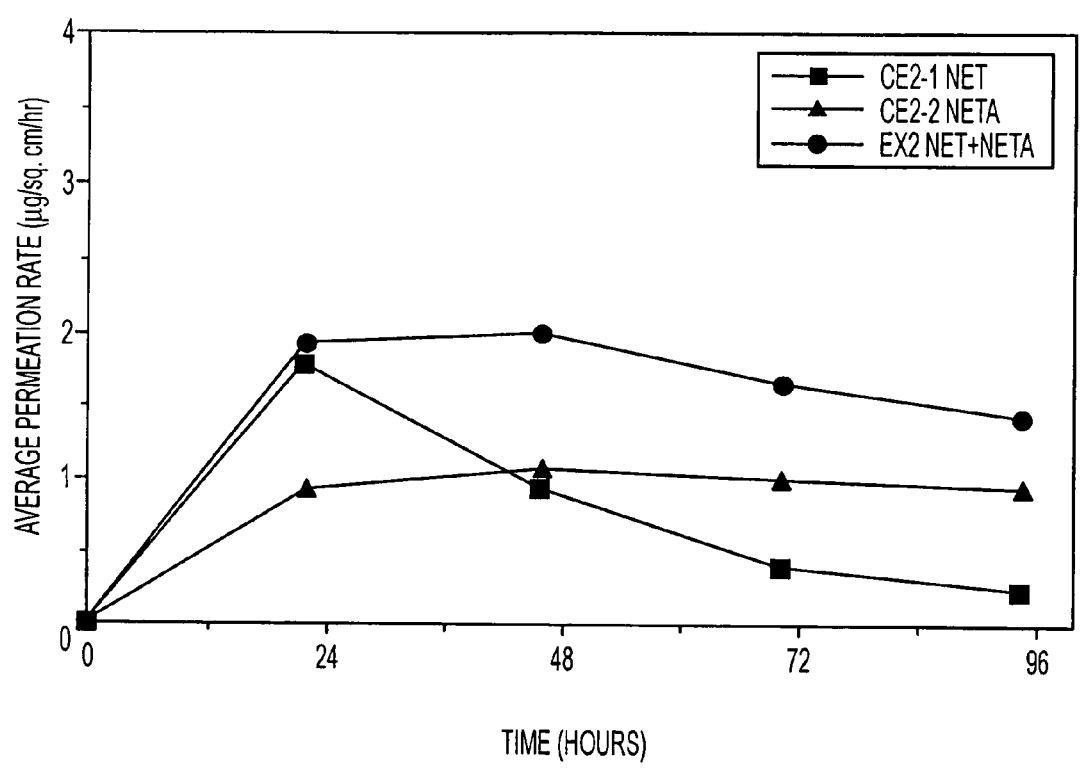
FIG. 2 is a graph illustrating the flux of norethindrone acetate from a composition containing norethindrone acetate and estradiol, combined norethindrone/norethindrone acetate from a composition containing norethindrone/norethindrone acetate and estradiol, and norethindrone from a composition containing norethindrone and estradiol.

Flux of the combined norethindrone/norethindrone acetate through the cadaver skin in vitro from the formulation of Example 2 is shown in FIG. 2 as circles (●). Also shown are comparative examples that contained only norethindrone and norethindrone acetate, which are shown as squares (■) and triangles (▲), respectively. As FIG. 2 indicates, the flux for the combined norethindrone/norethindrone acetate was significantly higher than either norethindrone or norethindrone acetate alone, in essentially in the same carrier composition.

Example 3 and Comparative Examples 3

A transdermal steroid/corresponding steroid derivative delivery composition was prepared with the following ingredients:

| | |
|---|---|
| testosterone | 6.0% |
| testosterone acetate | 3.0 |
| PVP Kollidon 30 | 12.0 |
| acrylic PSA (GMS788) | 5.0 |
| oleic Acid | 3.0 |
| dipropylene Glycol | 9.0 |
| silicone PSA (7-4603) | 63.4 |

Figure 3:
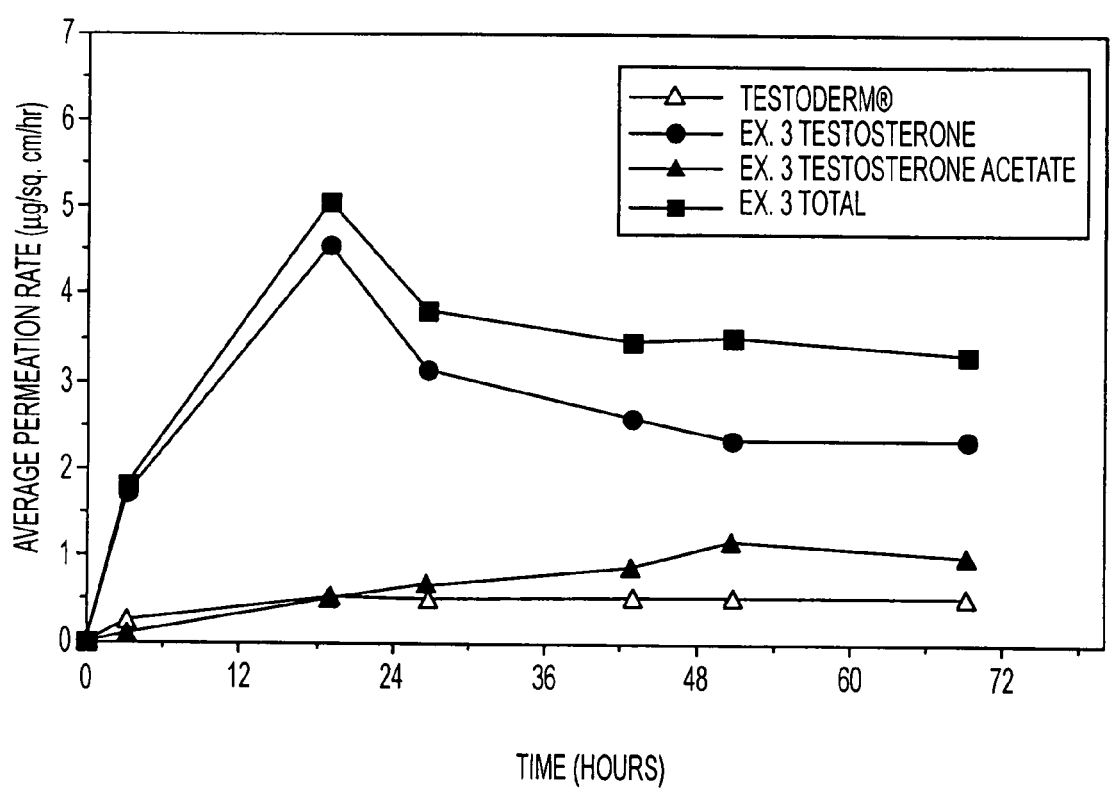
FIG. 3 is a graph illustrating the drug flux of combined testosterone/testosterone acetate from a composition containing testosterone/testosterone acetate, the flux of testosterone acetate from the same composition, the flux of testosterone from the same composition and the flux of testosterone from a transdermal drug delivery system called Testoderm 7 sold by Alza, Inc.
Figure 4:
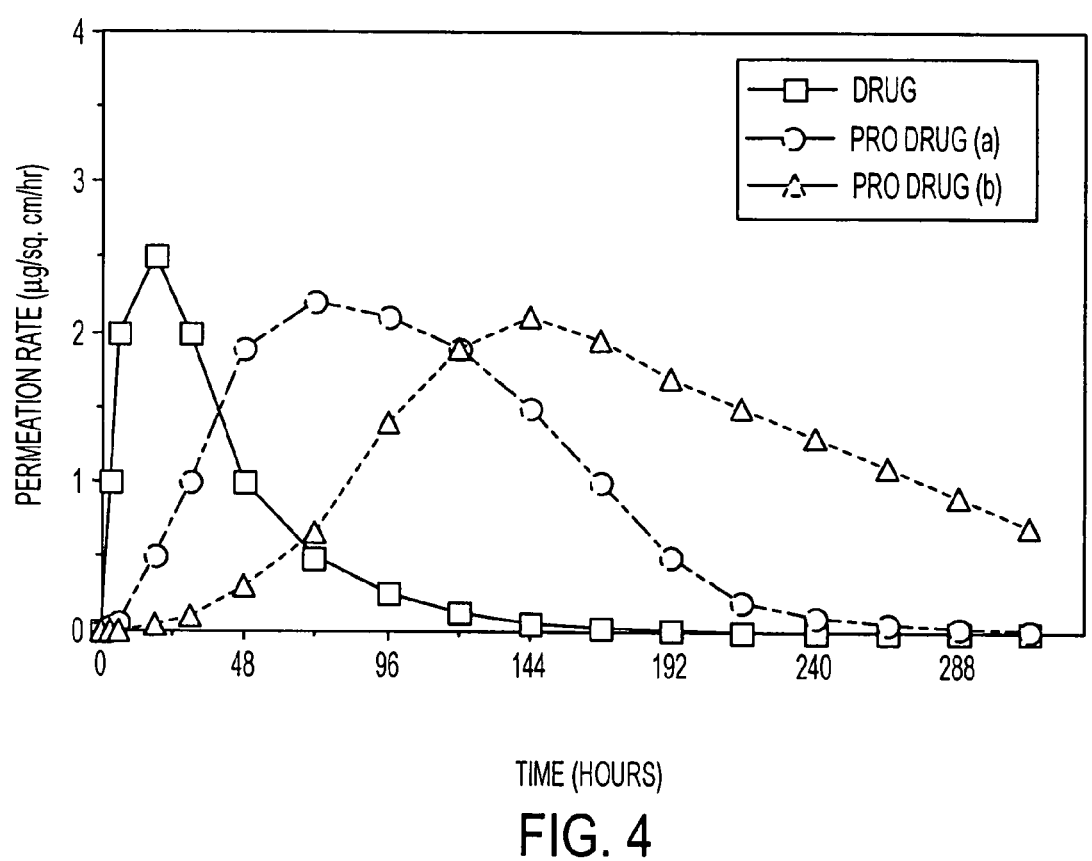
FIG. 4 is a graph illustrating drug and prodrug theoretical permeation from a single transdermal composition containing a parent drug and two prodrugs.

Flux of the combined testosterone/testosterone acetate through the cadaver skin in vitro from the formulation of Example 3 is shown in FIG. 3 as squares (■). Also shown are the separate flux of testosterone and testosterone acetate from the formulation of Example 3, shown as circles (●) and dark triangles (▲), respectively. Also shown is the flux of a commercially available testosterone composition sold under the trademark Testoderm7 sold by Alza, Inc., shown as open triangles (Δ). As FIG. 3 indicates, the flux for the combined testosterone/testosterone acetate of Example 3 was significantly higher than the Testoderm7 composition. Also, the individual fluxes of the testosterone and testosterone acetate of Example 3 were each greater than the flux of Testoderm7 and accordingly demonstrate that each drug entity is being delivered in an amount sufficient to provide a physiological effect.

Example 4 and Comparative Examples 4

Transdermal steroid/steroid derivative delivery compositions were prepared with the following ingredients:

|  | Ex 4-1 | Ex. 4-2 | Ex. 4-3 | Ex. 4-4 |
|---|---|---|---|---|
| Estradiol | 4% | 4% | 4% | 4% |
| Estradiol Acetate | 2.5 | — | — | — |
| Estradiol Enanthate | — | — | 2.5 | — |
| Estradiol Propionate | — | — | — | 2.5 |
| Kollidon 30 | 3 | 3 | 3 | 3 |
| Oleyl Alcohol | 6 | 6 | 6 | 6 |
| Dipropylene Glycol | 9 | 9 | 9 | 9 |
| Duro-Tak 87-2287 | 7 | 7 | 7 | 7 |
| Silicone PSA 7-4603 | 71 | 68.5 | 68.5 | 68.5 |

Examples 4-1 and 4-2 had crystals after 3 days. Examples 4-3 and 4-4 had no crystals at 13 days. From these results the acetate ester of estradiol is not as effective in inhibiting crystals, whereas, the propionate and enanthanate are effective in inhibiting crystals.

Examples 5-9

Transdermal parent drug/prodrug delivery compositions were prepared with the following ingredients:

| Ingredients (w/w %) | Ex. 5 | Ex. 6 | Ex. 7 | Ex. 8 | Ex. 9 |
|---|---|---|---|---|---|
| Polysiloxane PSA (BIO-PSA ® 7-4603) | 52 | 49 | 46 | 43 | 46 |
| Polyvinylpyrrolidone (Kollidon ® 30) | 25 | 25 | 25 | 25 | 25 |
| Oleic Acid | 5 | 5 | 5 | 5 | 5 |
| Dipropylene Glycol | 15 | 15 | 15 | 15 | 15 |
| Norethindrone | 3 | 3 | 3 | 3 | 0 |
| Norethindrone Acetate | 0 | 3 | 6 | 9 | 9 |

Figure 7:
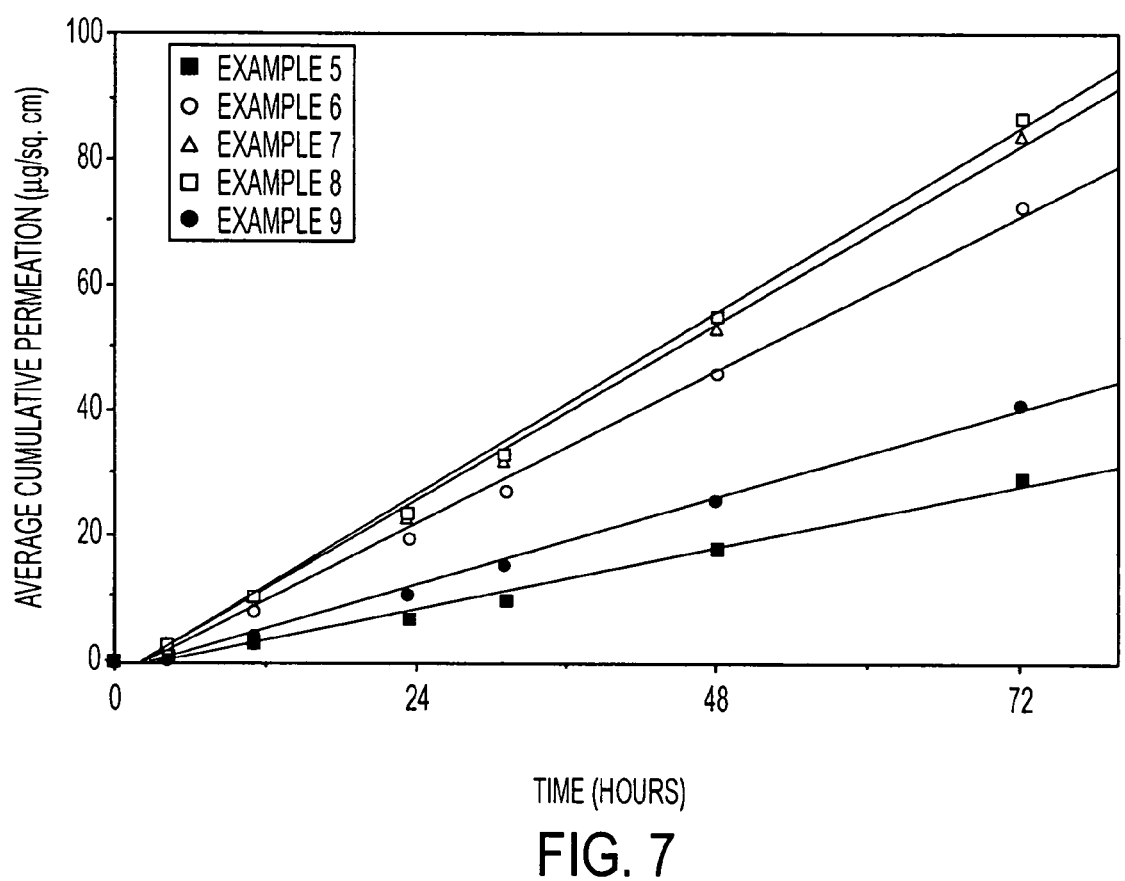
FIG. 7 shows combined cumulative permeation for norethindrone and norethindrone acetate for various combinations of parent drug/prodrug.

Examples 5 and 9 are comparative. The permeation rate of norethindrone/norethindrone acetate are shown in FIGS. 5-7. FIG. 5 shows the average cumulative permeation for norethindrone for Examples 5-8. FIG. 6 shows average cumulative permeation for norethindrone acetate for Examples 6-9. FIG. 7 shows average cumulative permeation for combined norethindrone and norethindrone acetate for Examples 5-9. All the figures show increased permeation for parent drug/prodrug combinations compared to the prodrug (in this case norethindrone acetate) or parent drug.

The formulations of Examples 6-8 were also tested for crystal formation. Each blend was cast onto a polyester release liner (ScotchPak® 1022; 3M, Minneapolis, Mich.) with a 15 ml wet gap applicator. The cast downs were air dried for five minutes at ambient temperature and humidity under a hood, and for an additional five minutes in a convection air oven at 92° C. to drive off any volatile solvents. Upon completion, the release liner coated with the dried drug mixture composition was laminated to the polyester side of a polyester/ethylene vinyl acetate backing material (ScotchPak® 9732; 3M, Minneapolis, Mich.). Individual units of 10 cm² were die cut and placed under a microscope for visual inspection at a magnification of 25×. The blends exhibited no crystal formation after 60 days.

It appears that a melting point depression is achieved by combining a parent drug and a prodrug, and this phenomenon likely accounts for crystal inhibition in such transdermal platforms.

Example 10

Figure 8:
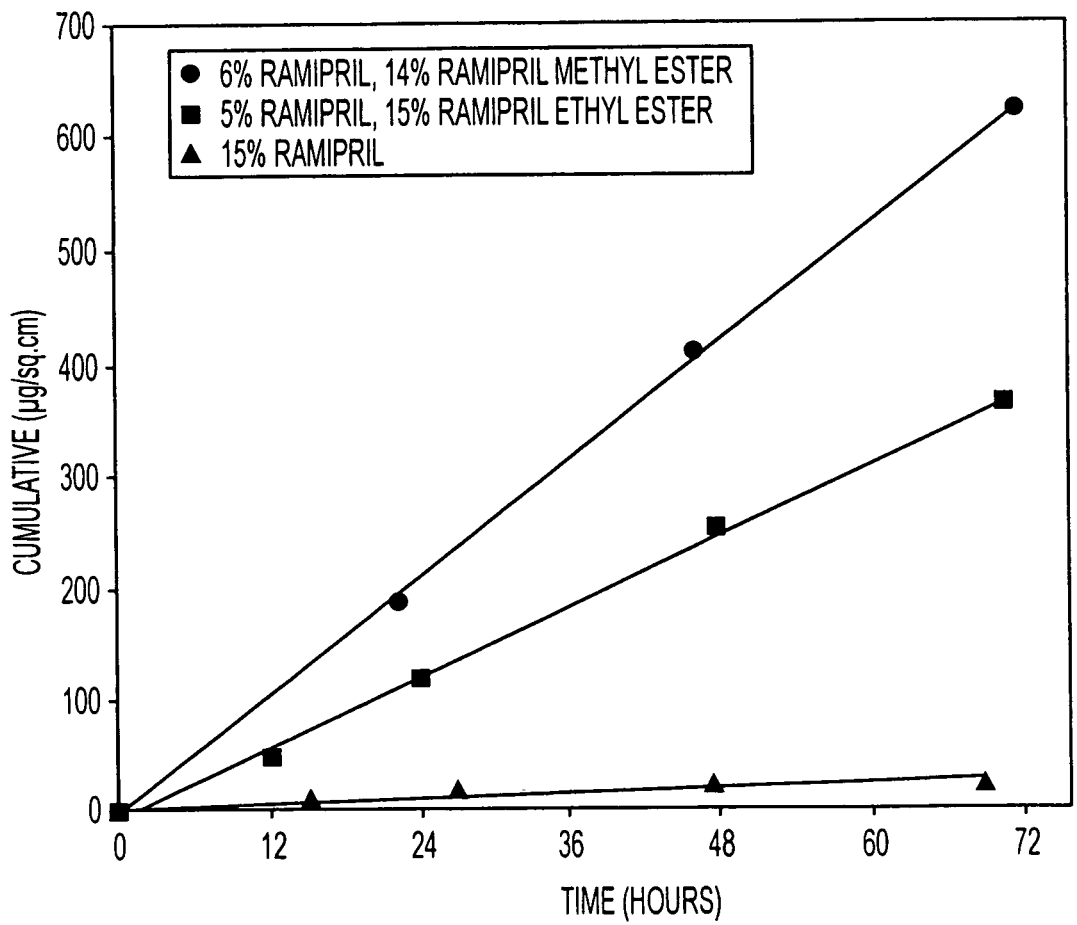
FIG. 8 shows cumulative permeation for ramipril and its prodrugs.
Figure 9:
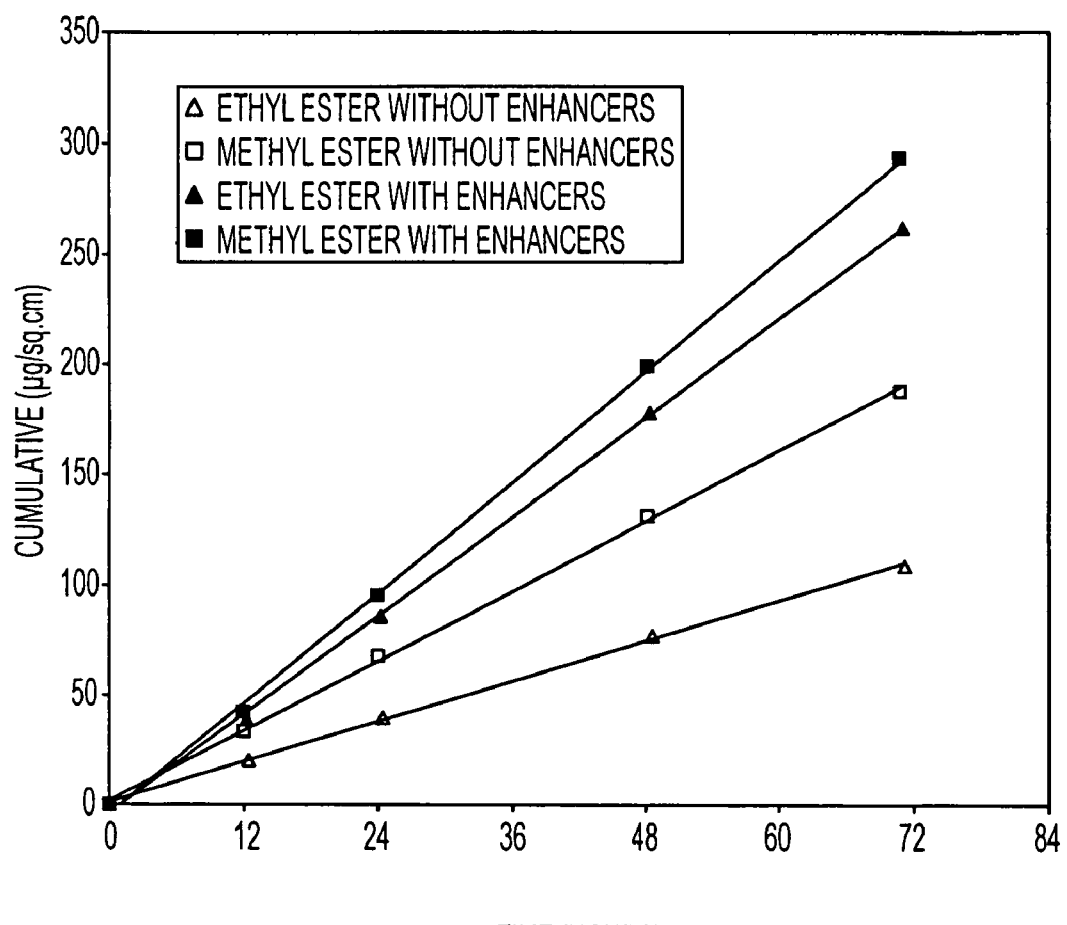
FIG. 9 shows cumulative permeation for ramipril prodrugs, with and without enhancers.

Prodrug effects on flux were also studied using an ace inhibitor drug, ramipril. Flux rates of two corresponding prodrugs—ramipril methyl ester and ramipril ethyl ester—were compared prior to combining with the parent drug. As shown in FIG. 9, without permeation enhancers, the methyl ester prodrug achieved a 73% higher flux than the ethyl ester prodrug in carrier formulations containing 20% drug, 20% polyacrylate adhesive (DURO-TAK® 87-90880, and 60% polysiloxane adhesive (BIO-PSA® 7-4102). With the addition of 3% oleyl alcohol and 5% dipropylene glycol to the formulations (reducing the polysiloxane adhesive to 52%), the flux was nearly doubled. In either event, the use of an ester prodrug in place of the parent drug can achieve, at the very least, over a 10 fold increase in flux (see ramipril flux (▲) in FIG. 8—only 15% ramipril could be solubilized without forming crystals—versus ramipril ethyl ester flux without enhancers (Δ) in FIG. 9). Use of non-functional or hydroxy functional adhesives are also preferred.

However, when both ramipril and a corresponding prodrug are combined in the formulations containing enhancers, an even higher flux can be obtained. As shown in FIG. 8, it was found that ramipril/prodrug combinations significantly improved flux with the methyl ester prodrug combination flux about doubling. In all formulations incorporating ramipril/methyl ester prodrug combinations, it was found that flux improved over either drug alone with the addition of the prodrug. Optimal flux at 20% drug concentration was found when the ratio of ramipril to the methyl ester prodrug was about 1:2.33, without significant improvement beyond a 1:3 ratio.

With ramipril/ethyl ester prodrug combinations, optimal flux at 20% drug concentration was achieved at a ratio of about 1:3 ramipril/prodrug and had about a 20% flux increase over ramipril ethyl ester alone. However, at about 1:1 ratio, it was found that flux actually decreased about 19% when compared to the flux of ramipril ethyl ester alone. Nonetheless, the ramipril/ethyl ester prodrug combination achieved a significant flux increase over ramipril alone. Accordingly, while it was found that ramipril/prodrug combinations provided improved flux over either drug entity alone, the ramipril methyl ester prodrug fluxed higher than the ethyl ester derivative.

While a number of preferred embodiments of the present invention have been described, it should be understood that various changes, adaptations and modifications may be made therein without departing from the spirit of the invention and the scope of the appended claims.

The invention claimed is:

1. A method for controlling the melting point of a drug used in a composition for transdermal delivery, comprising providing a pharmaceutically acceptable carrier comprising a pressure-sensitive adhesive and a combination of a drug and a corresponding pro-drug, wherein the drug/pro-drug combination begins to melt at a temperature that is lower than the melting points of each of the drug or pro-drug alone.

2. The method of claim 1, wherein the weight/weight ratio of pro-drug:drug is 1.

3. The method of claim 1, wherein the melting point of the pro-drug is lower than the melting point of the drug.

4. The method of claim 1, wherein the drug comprises a steroid and the pro-drug comprises a corresponding steroid derivative.

5. The method of claim 4, wherein the weight/weight ratio of steroid:corresponding steroid derivative is from 10:1 to 1:10.

6. The method of claim 4, wherein the corresponding steroid derivative is the steroid where the free hydroxy group at the 3, 11 or 17 position has been reacted with an alcohol moiety.

7. The method of claim 6, wherein the corresponding steroid derivative comprises the steroid where the free hydroxy group at the 17 position has been reacted with an alcohol moiety.

8. The method of claim 1, wherein the drug comprises norethindrone and the prodrug comprises norethindrone acetate.

9. The method of claim 8, wherein the weight/weight ratio of norethindrone acetate:norethindrone is 1:1.

10. The method of claim 1, wherein the drug comprises estradiol and the prodrug comprises estradiol 17-enanthate.

11. The method of claim 10, wherein the weight/weight ratio of estradiol 17-enanthate:estradiol is 1.

12. The method of claim 1, wherein the drug comprises estradiol and the pro-drug comprises a pro-drug selected from the group consisting of estradiol benzoate, estradiol 17-β-cypionate, estradiol 17-propionate, estradiol hemisuccinate (eutocol), estradiol enanthate, estradiol undecylate, estradiol acetate, estradiol proprionate and estradiol 3-methyl ether.

13. The method of claim 1, wherein the drug comprises testosterone and the pro-drug comprises a pro-drug selected from the group consisting of testosterone 17-β-cypionate, testosterone enanthate, testosterone nicotinate, testosterone phenylacetate, testosterone proprionate and testosterone 17-chloral hemiacetal.

14. The method of claim 1, wherein the drug comprises ramipril and the pro-drug comprises a pro-drug selected from the group consisting of ramipril methyl ester and ramipril ethyl ester.

15. The method of claim 1, wherein the drug comprises a progestin selected from the group consisting of allylestrenol, anagestone, desogestrel, dimethisterone, dydrogesterone, ethisterone, ethynodiol, gestodene, haloprogesterone, 17-hydroxy-16-methylene-progesterone, 17α-hydroxyprogesterone, lynoestrenol, medroxyprogesterone, melengestrol, norethindrone, norethynodrel, norgesterone, norgestimate, norgestrel, norgestrienone, norvinisterone, pentagestrone, and trimegestone.

16. The method of claim 1, wherein the drug comprises an anabolic steroid selected from the group consisting of androisoxazole, androstenediol, bolandiol, bolasterone, clostebol, ethylestrenol, formyldienolone, 4-hydroxy-19-nortestosterone, methandriol, methenolone, methyltrienolone, nandrolone, norbolethone, oxymesterone, stenbolone and trenbolone.

17. The method of claim 1, wherein the drug comprises an androgenic steroid selected from the group consisting of boldenone, fluoxymesterone, mestanolone, mesterolone, methandrostenolone, 17-methyltestosterone, 17α-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal and tiomesterone.

18. The method of claim 1, wherein the drug comprises an estrogen selected from the group consisting of conjugated estrogenic hormones, equilenin, equilin, estradiol, estradiol benzoate, estradiol 17-β-cypionate, estriol, estrone, and ethinyl estradiol.

19. The method of claim 1, wherein the drug comprises a glucocorticoid selected from the group consisting of 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone, Fluprednidene, Fluprednisolone, Flurandrenolide, Formocortal, Halcinonide, Halometasone, Halopredone, Hydrocortamate, Hydrocortisone, Mazipredone, Medrysone, Meprednisone, Methyolprednisolone, Mometasone Furoate, Paramethasone, Prednicarbate, Prednisolone, Prednisone, Prednival, Prednylidene, Tixocortal, and Triamcinolone.

20. The method of claim 1, wherein the drug comprises a mineralocorticoid selected from the group consisting of Aldosterone, Deoxycorticosterone and Fludrocortisone.

21. The method of claim 1, wherein the composition exhibits increased drug permeation as compared to a corresponding composition that does not comprise the pro-drug.

22. The method of claim 1, wherein the composition exhibits increased drug flux as compared to a corresponding composition that does not comprise the pro-drug.

23. The method of claim 1, wherein the composition exhibits increased non-crystallized drug loading as compared to a corresponding composition that does not comprise the pro-drug.

* * * * *

UNITED STATES PATENT AND TRADEMARK OFFICE
CERTIFICATE OF CORRECTION

Page 1 of 1

PATENT NO. : 8,110,565 B2
APPLICATION NO. : 11/979263
DATED : February 7, 2012
INVENTOR(S) : Houze et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 387 days.

Signed and Sealed this
Thirteenth Day of November, 2012

David J. Kappos
*Director of the United States Patent and Trademark Office*